United States Patent
Czygan et al.

(10) Patent No.: US 7,702,389 B2
(45) Date of Patent: Apr. 20, 2010

(54) CARDIAC PACEMAKER

(75) Inventors: Gerald Czygan, Buckenhof (DE); Michael Lippert, Ansbach (DE)

(73) Assignee: Biotronik CRM Patent AG (CH)

( * ) Notice: Subject to any disclaimer, the term of this patent is extended or adjusted under 35 U.S.C. 154(b) by 705 days.

(21) Appl. No.: 11/559,626

(22) Filed: Nov. 14, 2006

(65) Prior Publication Data

US 2007/0150012 A1 Jun. 28, 2007

(30) Foreign Application Priority Data

Dec. 23, 2005 (EP) .................. 05028351

(51) Int. Cl.
*A61N 1/00* (2006.01)

(52) U.S. Cl. ........................................ 607/9

(58) Field of Classification Search ............ 600/547; 607/9, 7
See application file for complete search history.

(56) References Cited

U.S. PATENT DOCUMENTS

| | | | |
|---|---|---|---|
| 6,223,082 B1 | 4/2001 | Bakels et al. | |
| 7,228,174 B2* | 6/2007 | Burnes et al. | 607/17 |
| 2005/0049646 A1 | 3/2005 | Czygan et al. | |
| 2008/0249583 A1* | 10/2008 | Salo et al. | 607/11 |

FOREIGN PATENT DOCUMENTS

WO PCT/03/10074 * 4/2003

WO 03/092804 A1 11/2003

OTHER PUBLICATIONS

Search Report of the European Patent Office dated May 31, 2006 for European application No. 05028351.4.

* cited by examiner

*Primary Examiner*—George Manuel
*Assistant Examiner*—Robert N Wieland
(74) *Attorney, Agent, or Firm*—Craig A. Fieschko, Esq.; DeWitt Ross & Stevens S.C.

(57) ABSTRACT

The invention concerns implantable cardiac stimulation devices in general which have at least one stimulation pulse generator (A-STIM; RV-STIM; LV-STIM) to selectively generate a stimulation pulse for delivery to one of at least two different chambers of a heart, said chambers include right and left atria and right and left ventricles, at least one impedance measuring stage (I, U, IMP) being connected to electrodes or connectors for such electrodes to measure an intracardiac impedance when in use, a control unit (CTRL) connected to the stimulation pulse generator and to the impedance measuring unit and being adapted to process a minimum impedance value for a heart cycle to trigger stimulation pulses for two different chambers of the heart with an adjustable time delay (VVD; AVD) and to adjust said time delay depending upon the measured intracardiac impedance minimum value. According to the invention the control unit is adapted to adjust the time delay such that the minimum value of the intracardiac impedance during one heart cycle is minimized or such that the AVD delay is equal to the time interval between an atrial event and the point of time when the minimum impedance value occurs after said atrial contraction.

17 Claims, 11 Drawing Sheets

CARDIAC PACEMAKER

Figure 1A:
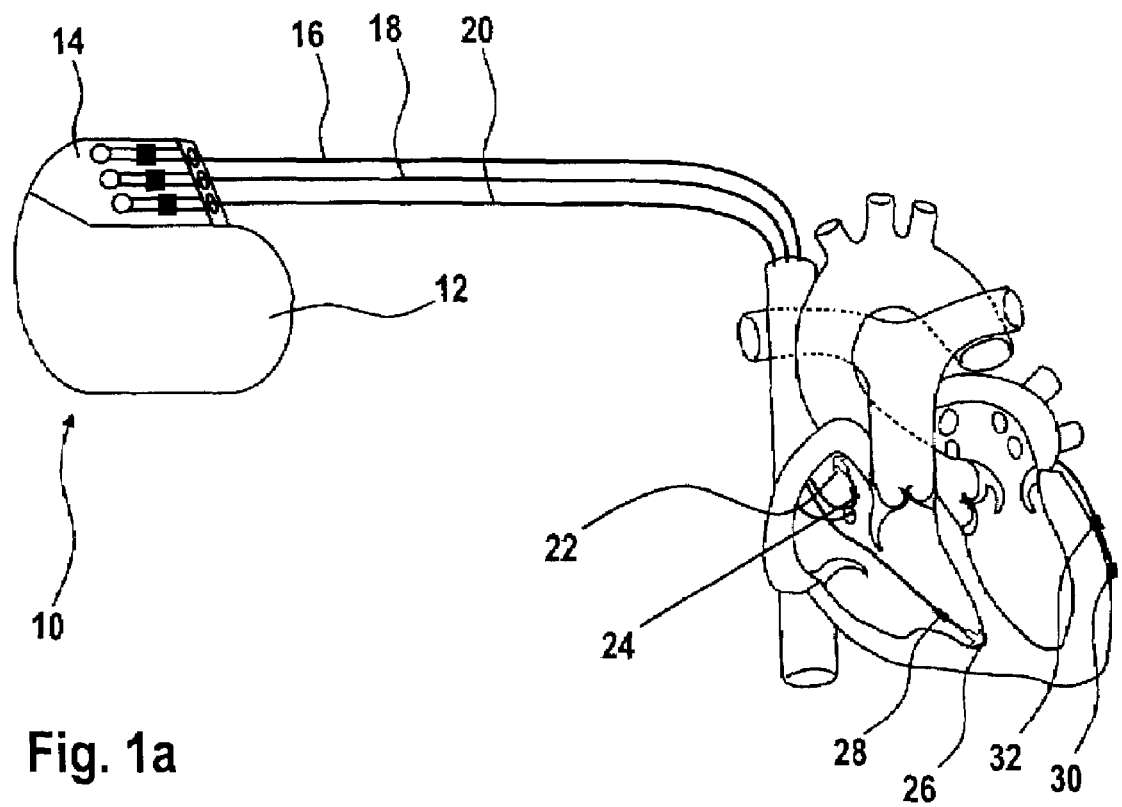

The invention relates generally to electrotherapeutic devices such as a cardiac pacemaker or an implantable cardioverter-defibrillator, which will be called "pacemaker" for the purpose of this description. The pacemaker preferably is an implantable pacemaker.

The pacemaker has at least one stimulation pulse generator to selectively generate stimulation pulse for delivery to at least two different chambers of a heart, said chambers include right and left atria and right and left ventricles. Said one stimulation pulse generator may be switchable in order to generate stimulation pulses for different chamber of the heart. In general, however, separate stimulation pulse generators will be provided for each heart chamber to be stimulated.

Further, the pacemaker includes at least one impedance measuring stage being connected to electrodes or a connector for such electrodes to measure an intracardiac impedance when in use. The pacemaker has a control unit connected to the stimulation pulse generator and to the impedance measuring unit. The control unit is adapted to trigger stimulation pulses for two different chambers of the heart with an adjustable time delay. The time delay may be an atrioventricular time delay (AVD) between an atrial event and a ventricular event and/or an interventricular delay (VVD) between a right ventricular event and a left ventricular event.

The pacemaker includes means to optimize said atrioventricular and/or said interventricular delay based on a hemodynamic sensor information.

For AVD optimization the pacemaker provides for at least one atrial and one ventricular channel for pacing and/or sensing. For VVD optimization the pacemaker provides for pacing channels for both ventricles.

A pacemaker shall help a heart suffering from some disorder to perform similar to healthy heart.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the right atrium contracts and forces the blood that has accumulated therein into the ventricle. The natural stimulus causing the right atrium to contract is conducted to right ventricle via the atrioventricular node (AV node) with a short, natural delay, the atrioventricular delay (AV-delay). Thus a short time after the right atrial contraction (a time sufficient to allow the bulk of the blood in the right atrium to flow through the one-way valve into the right ventricle), the right ventricle contracts, forcing the blood out of the right ventricle to the lung. A typical time interval between contraction of the right atrium and contraction of the right ventricle might be 100 ms; a typical time interval between contraction of the right ventricle and the next contraction of the right atrium might be 800 ms. Thus, it is an right atrial contraction (A), followed by a relatively short time thereafter by a right ventricle contraction (V), followed a relatively long time thereafter by the next right atrial contraction, that produces the desired AV synchrony. Where AV synchrony exists, the heart functions very efficiently as a pump in delivering life-sustaining blood to body tissue; where AV synchrony is absent, the heart functions as an inefficient pump (largely because the right ventricle is contracting when it is not filled with blood).

Similarly, the left ventricle contracts in synchrony with left and right atrium and the right ventricle with a positive or negative time delay between a right ventricular contraction and a left ventricular contraction.

A pacemaker generally shall induce a contraction of a heart chamber by delivery of a stimulation pulse (pacing pulse) to said chamber when no natural (intrinsic) contraction of said chamber occurs in due time. A contraction of a heart chamber often is called "event". Since a contraction may be an intrinsic contraction, which can be sensed by an according sensing stage of a pacemaker, such event is called a sensed event. A contraction due to delivery of a stimulation pulse is called a paced event. A sensed event in the atrium is called As, a paced atrial event is called Ap. Similarly, a sensed event in the ventricle is called Vs and a paced ventricular event is called Vp.

To mimic the natural behavior of a heart, a dual-chamber pacemaker provides for an AV-delay timer to provide for an adequate time delay (AV-delay, AVD) between a natural (intrinsic) or a stimulated (paced) right atrial contraction and a right ventricular contraction. In a similar way a biventricular pacemaker provides for an adequate time delay (VV-delay, VVD) between a right ventricular contraction and a left ventricular contraction.

The time delay for a left ventricular (stimulated, paced) contraction may be timed from a scheduled right ventricular contraction which has not yet occurred or from a natural (intrinsic) or a stimulated (paced) right atrial contraction. A left ventricular stimulation pulse is scheduled by a time interval AVD+VVD.

To deal with possibly occurring natural (intrinsic) atrial or ventricular contractions, a demand pacemaker schedules a stimulation pulse for delivery at the end of the AV-delay or the VV-delay, respectively. The delivery of said stimulation pulse is inhibited, if a natural contraction of the heart chamber to be stimulated is sensed within the respective time delay.

Ventricular pacing in one or both ventricles is required for patients with AV-block and for CHF patients that are indicated for resynchronization therapy. For patients with intact sinus rhythm or with effective atrial pacing it is beneficial to stimulate the ventricle(s) synchronous with the atrial activation, i.e., after a certain delay period after the atrial event. Standard AV-synchronous dual- or three-chamber implantable devices have a programmable AVD that can be adjusted by the physician. Several studies have shown the importance of individual AVD optimization to improve the cardiac output. Especially for CHF patients an optimization of the AVD is essential. As the pumping efficacy is impaired, the optimal timing of the ventricular stimulus in relation to the atrial event contributes significantly to the cardiac performance. If the AVD is too short, the ventricle contracts before it is completely filled by the atrial blood inflow. The active filling time is reduced. Hence the stroke volume and the cardiac output is reduced. If the AVD is too long, the ventricle contracts a while after the completion of atrial contraction. Hence the passive filling time of the ventricle, i.e., the diastolic filling period during the myocardial relaxation before the atrial kick, is decreased. Also backflow of blood from the ventricle into the atrium is likely. Thus also in this case the CO is reduced. Similar to the heart rate also the optimal AVD depends on the activation state of the circulation. If the sympathetic tone is high, e.g., during exercise, the optimal AVD is shortened compared to the resting value.

Patients with CHF and LBBB, i.e., with interventricular dyssynchrony expressed by a widened QRS complex may benefit from biventricular pacing. Pacing both ventricles simultaneously or with a certain VVD restores the synchrony of the ventricles and thus improves the hemodynamic performance. Also mitral regurgitation is reduced by biventricular pacing. Recent CRT pacing devices, IPGs or ICDs, offer a programmable VVD parameter. The delay time between the RV and LV stimulation can be programmed, usually approx. in the range −100 ms . . . +100 ms. The sign determines whether the RV or the LV is paced first. 0 ms means simultaneous pacing of both ventricles. Also RV or LV-only pacing can be programmed. It has been found that the setting resulting in optimal hemodynamics varies patient individually. The optimal value also depends on the individual position of the left ventricular pacing lead which usually is located in a lateral coronary vein or in rare cases on the left epicardium.

Several methods for individual AVD optimization are state of the art. The adjustment of AVD in most cases is performed during the follow-up procedure by the physician with external measurement systems, not by the implant itself. In most of the methods the patient is in rest during the adjustment procedure and only the 'static' AVD is optimized. Although modern pacing devices possess a programmable dynamic AVD, i.e., an AVD that depends on the heart rate, the dynamic values are estimated in the majority of cases.

The following methods for AVD optimization have been proposed among others:
External non-invasive methods:
  echocardiography:
    determination of maximal LVSV or CO,
    determination of optimal timing, i.e., end of AVD after end of mitral flow (Dopplerecho Awave),
  impedance cardiography:
    determination of maximum LVSV/CO,
  finger plethysmography.
External invasive or minimal invasive methods:
  invasive LV pressure:
    determination of maximum contractility, i.e., maximum LV dp/dtmax
  invasive aortic pulse pressure:
    determination of max. pulse pressure (the aortic pulse pressure reflects the LVSV)
  measurement of ANP hormone plasma level:
    determination of minimum plasma level (determined approx. a week after programming).

Although especially echo-based methods are frequently used in clinical practice, it is disadvantageous that there is no continuous optimization and that the optimization is only performed under rest conditions in supine position. Some methods have been proposed that use sensors, which are integrated into the implant. Study data have been published to test the feasibility of AVD optimization based on such sensors. Several patents exist disclosing sensor based methods. In clinical practice the sensors again are basically used for determination of the best AVD during a follow-up investigation or for research.

The following sensor methods were published:
Implant sensor methods:
  PEA: determination of the sigmoid inflection point of the PEA=f(AVD) curve
  RV pressure: determination of the lowest ePAD
  QT-interval: determination of the maximum evoked QT-interval
  unipolar impedance: determination of max. absolute derivative
  intracardiac electrogram: computation of the optimum left AVD from the intrinsic interatrial and interventricular conduction delays, it is also proposed to estimate those values from noninvasive ECG tracings.

The main disadvantage of the non-invasive methods is that the optimization cannot be performed continuously but only during the follow-ups when the patient is in the hospital or in the outpatient clinic. Also only the AVD at rest can be determined. The same is true for the invasive methods. The disadvantage of the PEA and the pressure methods is that a special pacing lead with an embedded acceleration or pressure sensor is required.

Regarding the prior methods for WD optimization, several methods for individual VVD optimization have been proposed. The adjustment mainly is performed during the follow-up procedure by the physician with external measurement systems, not by the implant itself. The methods for optimizing the VVD are similar to those used for AVD optimization. Much less investigations are published than for AVD adjustment.

External non-invasive methods:
  echocardiography
    determination of maximal LVSV or CO,
    minimization of mitral regurgitation
    determining the optimal synchronization by TDI.
External invasive or minimal invasive methods:
  invasive LV pressure: determination of maximum contractility, i.e., maximum LV $dp/dt_{max}$
  invasive aortic pulse pressure: determination of max. pulse pressure Also, optimization of the AV-Delay or the VV-Delay, respectively, based on determination of the cardiac output (CO) or stroke volume (SV) via measurement of the intracardiac impedance is known; see for example WO 03/051457.

In view of the prior art it is an object of the invention to provide a cardiac pacemaker with improved means for optimization of a time delay such as AVD or VVD.

This object of AVD-optimization is achieved by a cardiac pacemaker as introduced at the very beginning of this description having a control unit which is adapted to adjust said time delay depending upon a minimum impedance value for a heart cycle such that the adjusted time delay results in a minimal minimum value of the intracardiac impedance (i.e., the maximum volume). In other words: the control unit adjusts the time delay such that the minimum of the impedance in a heart cycle becomes minimal.

For the optimization of the VVD the control unit adjusts the time delay in a way that the minimum of the impedance in a heart cycle becomes maximal.

In contrast to prior art devices as for example disclosed in WO 03/051457 it is not the difference between the maximum value and the minimum value of the intracardiac impedance during one heart cycle reflecting stroke volume or cardiac output, respectively, that is maximized. Instead, the pacemaker according to the invention relies solely on the minimum value of the intracardiac impedance for optimization of the time delay.

The invention is based on the inventor's insight that AVD is to be adjusted such that a maximum diastolic filling of the left ventricle is achieved, i.e., a maximum of the left ventricle end diastolic volume (LVEDV). Increasing the LVEDV under otherwise constant conditions also increases the SV and hence the CO due to the autoregulation of the heart, the so-called Frank-Starling mechanism. The adjusted AVD of the pacing device is considered to be optimal when the LVEDV is maximal. To reach this target either the right heart AVD or the left heart AVD of a three-chamber pacer can be optimized. The goal is the same: maximizing the LVEDV. The LVEDV is assessed by measuring the left ventricular end diastolic impedance (LV EDZ). The highest LVEDV corresponds with the lowest EDZ.

In the prior art, AVD optimization by maximizing the left ventricular stroke volume (LVSV) has been proposed, see inter alia U.S. Pat. No. 6,223,082.

The advantage of the LVEDV based method according to the present invention over a LVSV based method is that LVEDV (LVEDZ) based optimization of the AVD is not influenced by mitral regurgitation.

In the prior art devices, the impedance sensor can only determine the total LVSV, i.e., the volume that is pumped out of the LV. It can not differentiate whether the blood is carried into the aorta or back into the LA.

The goal of the VVD optimization algorithm is to optimize the systolic blood ejection from the LV into the aorta by optimal interventricular synchronization, i.e., to minimize the LVESV and the mitral regurgitation.

Alternative approaches to optimize the systolic function by optimizing the WD could be based on minimizing the left ventricular end systolic volume (LVESV) or maximizing the LVSV. However, the disadvantage of these alternative approaches again is that the adjustment of WD would be affected by the mitral regurgitation, that is included in the total SV. If, in contrast, the transient change in LVEDV is observed immediately upon a change of the VVD (only the first few beats), it will reflect mainly the changed ability of the systole to pump blood out of the ventricle, thus leaving a different amount of blood in the ventricle for the next cycle. Therefore, e.g., upon an increased "forward" SV (due to reduced mitral regurgitation), the LVEDV of the next cycle will be smaller than in the preceding cycle (by the amount by that the SV has been increased). This "transient method" allows an optimization of the VVD in order to reduce mitral regurgitation.

Preferably, the cardiac pacemaker provides for an impedance measuring stage that is adapted to perform an impedance measurement in a quadrupolar configuration using two poles for current injection and another two poles for voltage measurement. It has turned out that thus reliable intracardiac impedance values can be obtained.

In a preferred embodiment of the pacemaker the control unit is adapted to perform a test measurement wherein an average minimum impedance value (EDZ_avg) is determined for a time delay to be tested by applying said time delay (AVD(i); VVD(i)) to be tested for a predetermined number of preferably 10 cardiac cycles measuring the minimum impedance value thus achieved for each cardiac cycle and forming an average minimum impedance value (EDZ_avg) from the measured minimum impedance value associated with said time delay to be tested.

A predefined set of time delays to be tested is preferably stored in a memory of the cardiac pacemaker.

In another preferred embodiment of the cardiac pacemaker the control unit is adapted to perform several test measurements for different time delays to be tested. Preferably the control unit is adapted to compare different average minimum impedance values associated with different time delays resulting from aforementioned measurements and to determine an optimal time delay being associated with the smallest of all average impedance values (Min(EDZ_avg)) resulting from the test measurements.

In order to allow for a better adaptation of the adjusted time delay to different states of exertion, the cardiac pacemaker can provide for a control unit which is adapted to perform a reference measurement by which a reference minimum impedance value (EDZ_avg) is determined for a fixed reference time delay by applying said reference time delay (AVD_ref; VVD_ref) for a predetermined number y of cardiac cycles measuring the minimum impedance value (EDZ_ref) thus achieved for each cardiac cycle and forming an average reference minimum impedance value (EDZ_ref_avg) from the measured minimum impedance value associated with said fixed reference time delay.

By such reference measurement a kind of exertion dependent baseline for time delay optimization is obtained.

In a preferred embodiment, the cardiac pacemaker will use such baseline measurement by having a control unit which is adapted to perform both, a test procedure including a reference measurement and a test measurement, and to determine a difference impedance value ($\Delta$EDZ) between the reference average minimum impedance value (EDZ_ref_avg) resulting from said reference measurement and the average minimum impedance value (EDZ_avg) resulting from said test measurement being associated with a time delay to be tested. Preferable, the control unit is adapted to repeat said test procedure for different time delays to be tested and to compare different of said difference impedance values associated to different time delays to be tested and to determine an optimal time delay being associated with largest of all difference impedance values (Max($\Delta$EDZ)) resulting from the test procedures.

Preferably, the time delay to be optimized is an AV-delay (atrioventricular delay) a VV-delay (interventricular delay) or both.

In a particular embodiment of the cardiac pacemaker a control unit is provided which is adapted to perform an AVD test procedure including the steps of forming an average impedance curve determining the duration of a time interval from an atrial event to the point of time when the average impedance curve reaches its minimum and assigning said time duration as value for the optimal atrioventricular time delay (AVD_opt).

Thus, an optimized (adjusted) AV-delay can be directly derived from the time course of impedance. In general, the time course of impedance being evaluated needs not necessarily to be an averaged time course. However, averaging the time course avoids problems which could arise from ectopic contractions and other interference.

Regarding optimization of the W delay the inventors have made the following observation: When the synchronization is optimal for an individual patient due to a certain WD and the LVESV is minimal, it is expected that the LVEDV will decrease for the first few heart beats after programming that better WD value. The reason for the decreased LVEDV for the first few cycles is that more blood is pumped from the LV into the circulation. It will take some cycles then until this blood reaches the ventricle again through the venous system. I.e., for the first few beats the LVEDV is decreased even with a better synchronization. Consequently the EDZ is increased.

As a consequence, in a preferred embodiment of the invention, test measurement delay means are provide which cause time between starting an application of a VV delay to be tested and said test measurements for determining an optimal W delay. Such time delay may include a limited number of 3 to 6 heart cycles.

The invention shall now be further illustrated by way of example embodiments as shown in the figures.

FIG. 1a: shows an implantable biventricular pacemaker according to the invention with electrode leads connected thereto. The position of the electrodes in a human heart are illustrated as well.

Figure 1B:
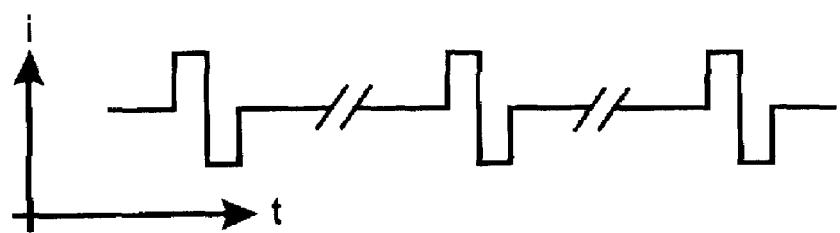
Figure 2A:
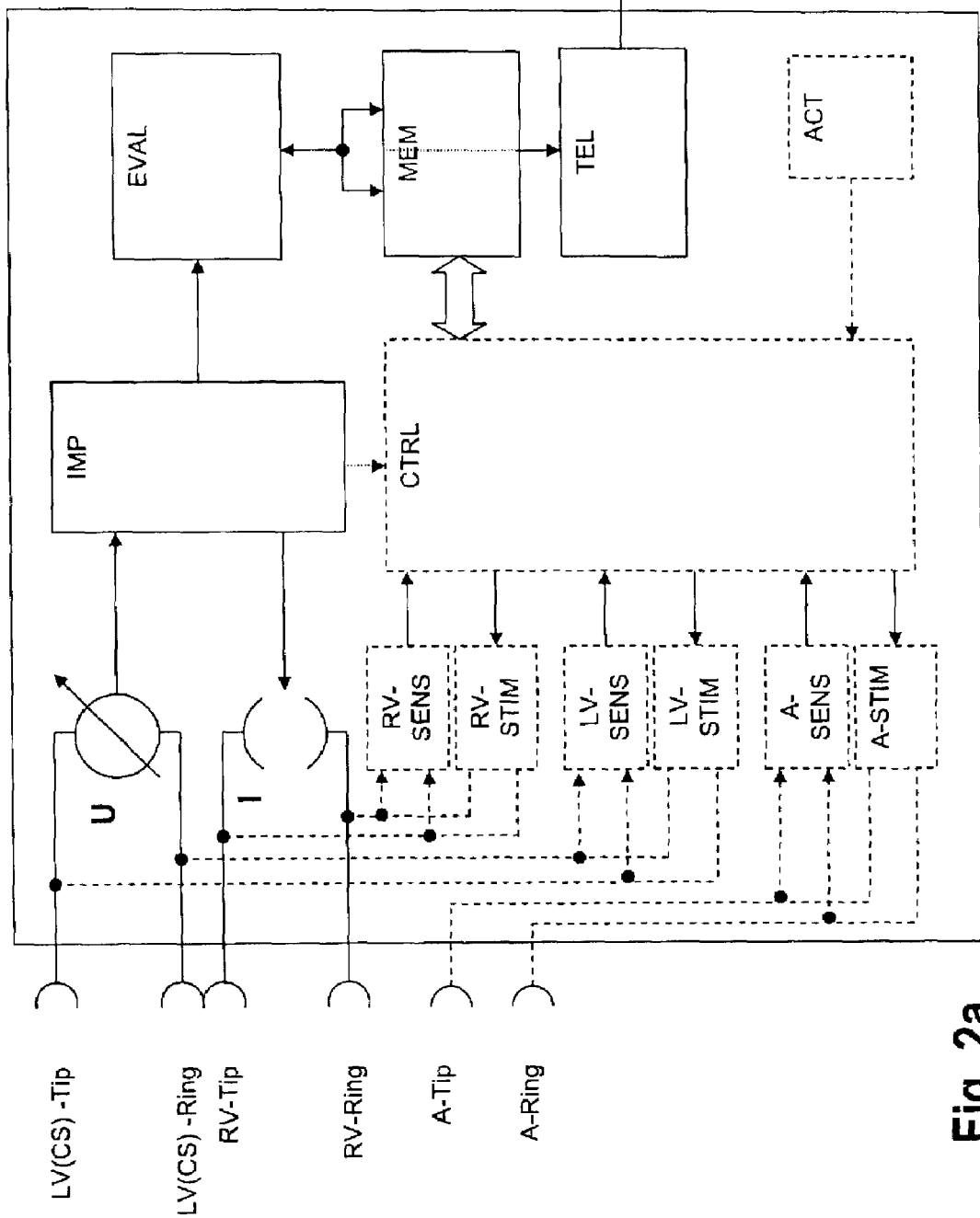
Figure 2B:
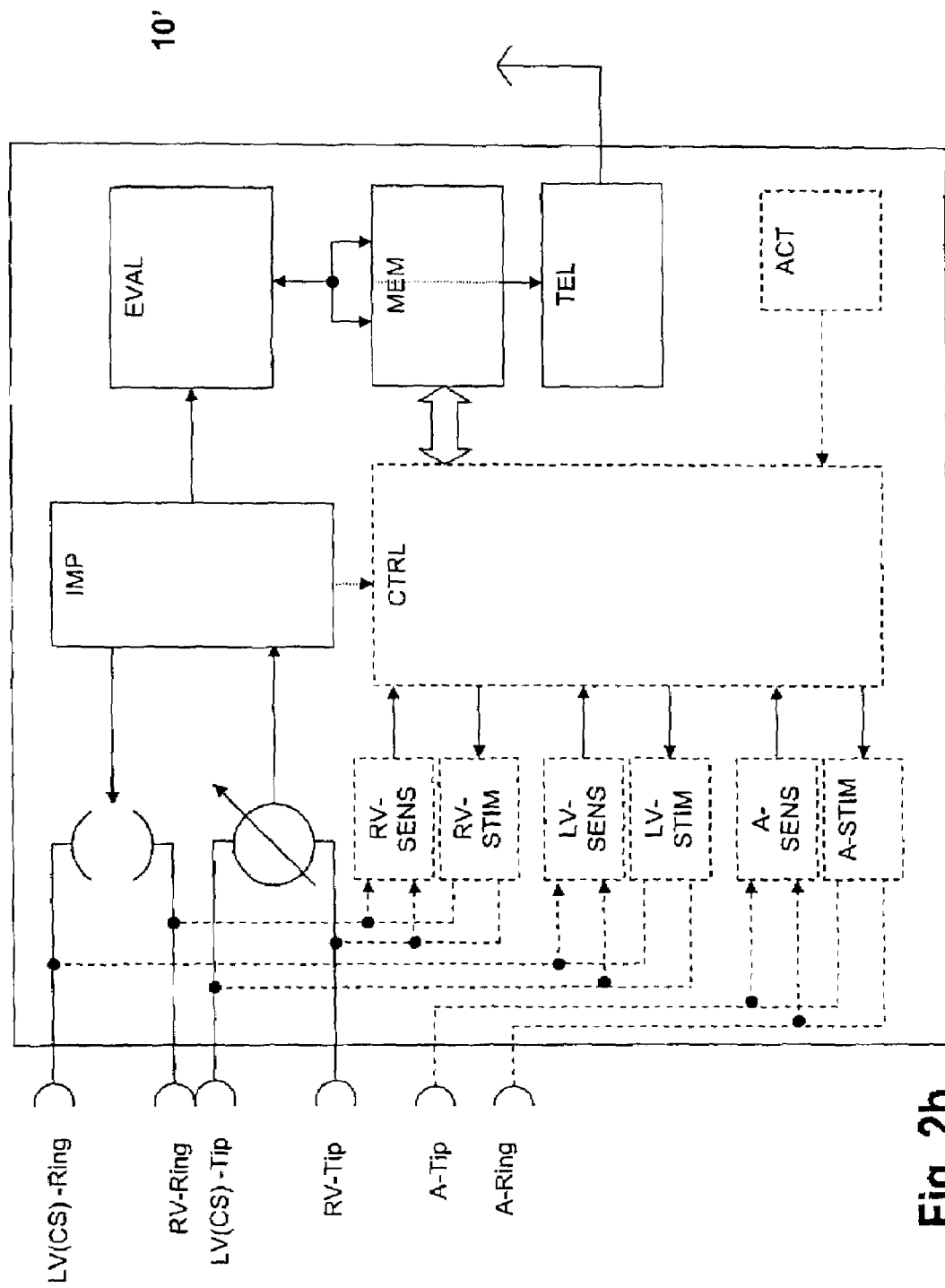
Figure 2C:
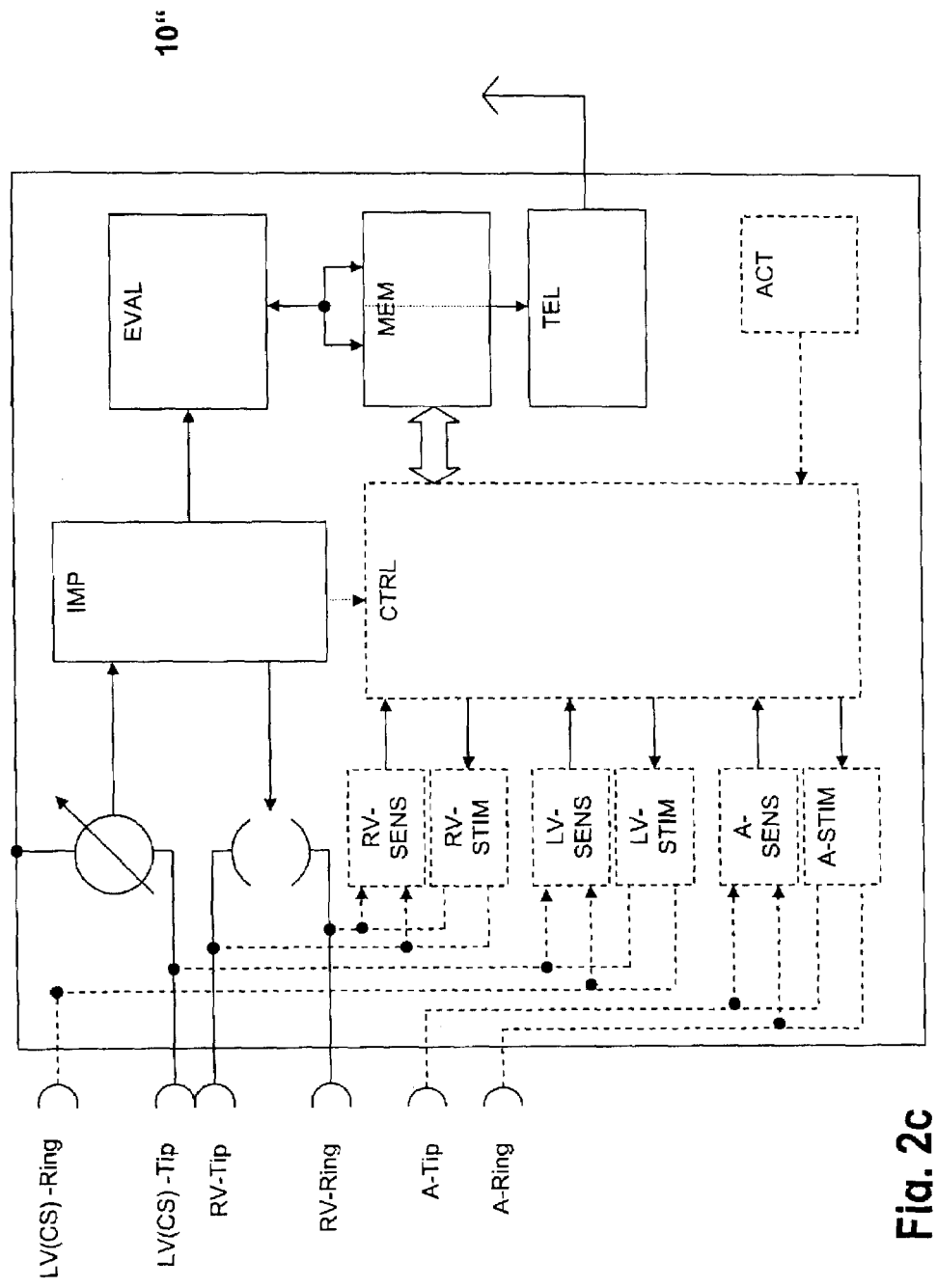
Figure 3A:
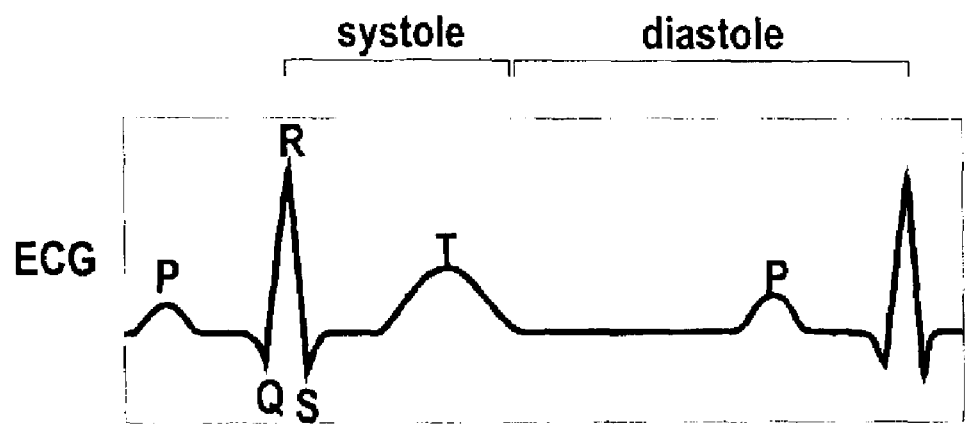
Figure 3B:
Figure 3C:
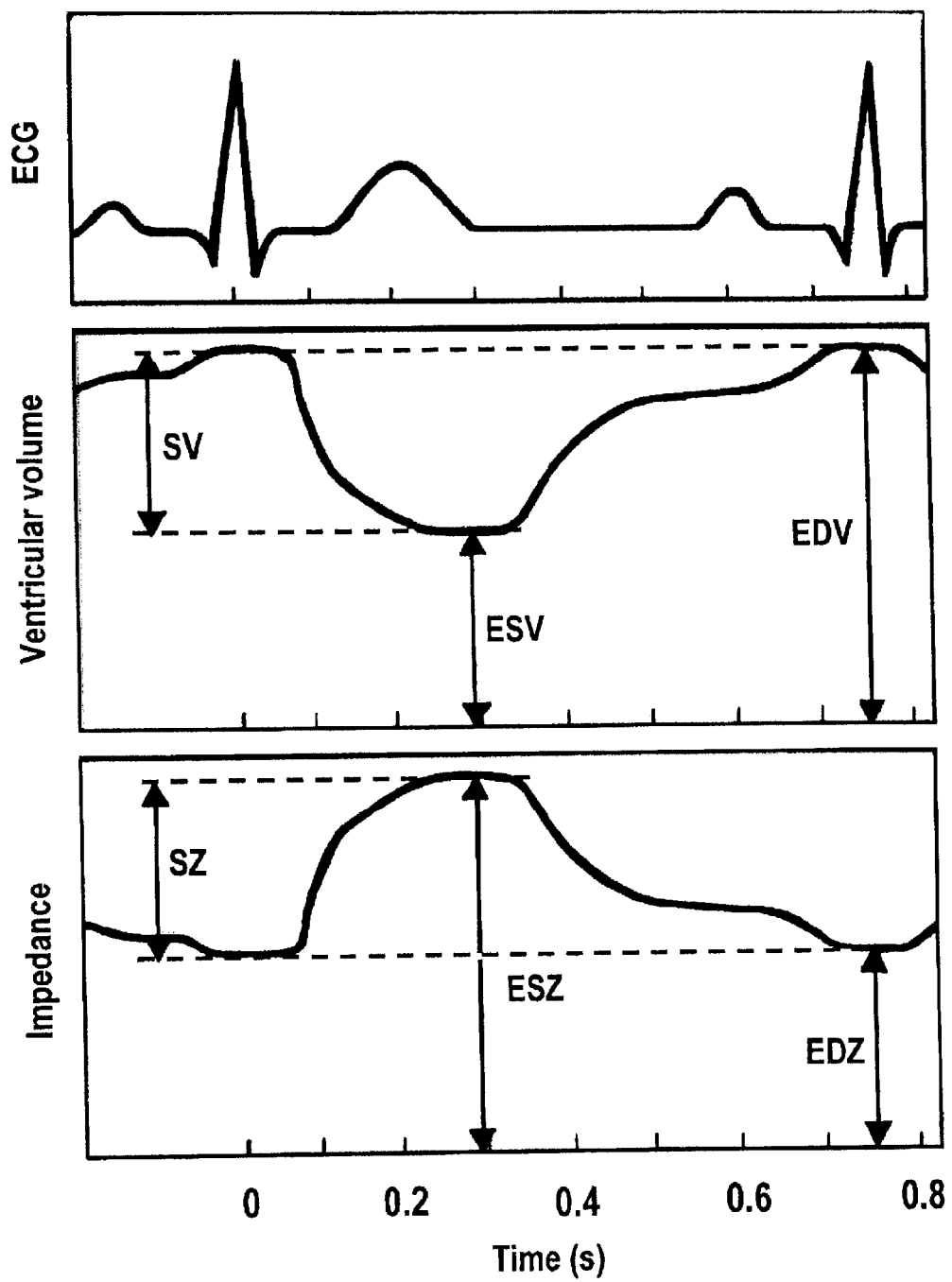
Figure 4:
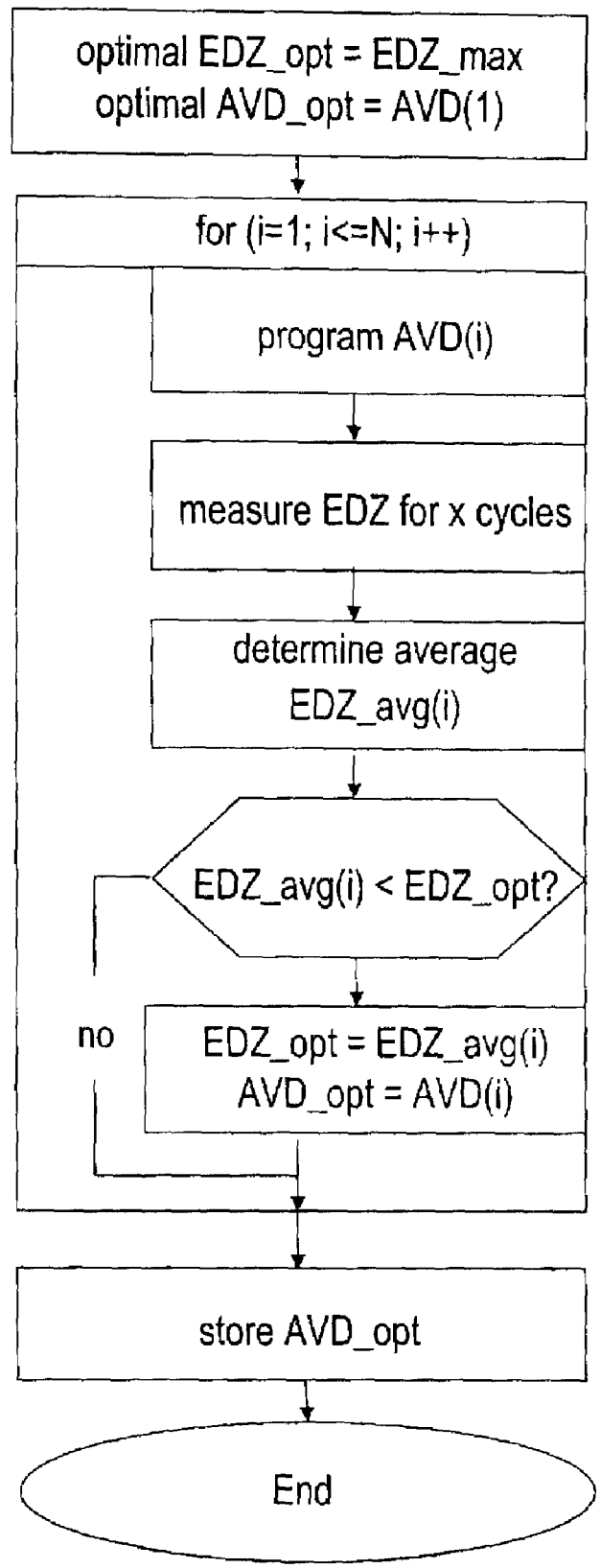
Figure 5:
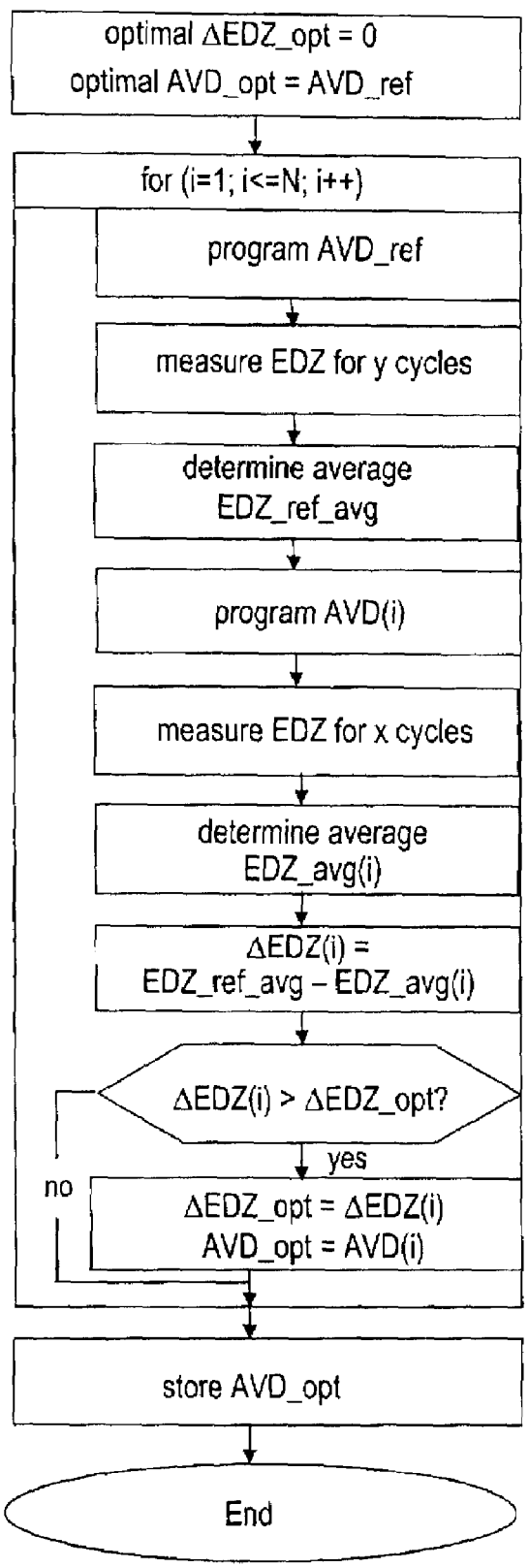
Figure 6:
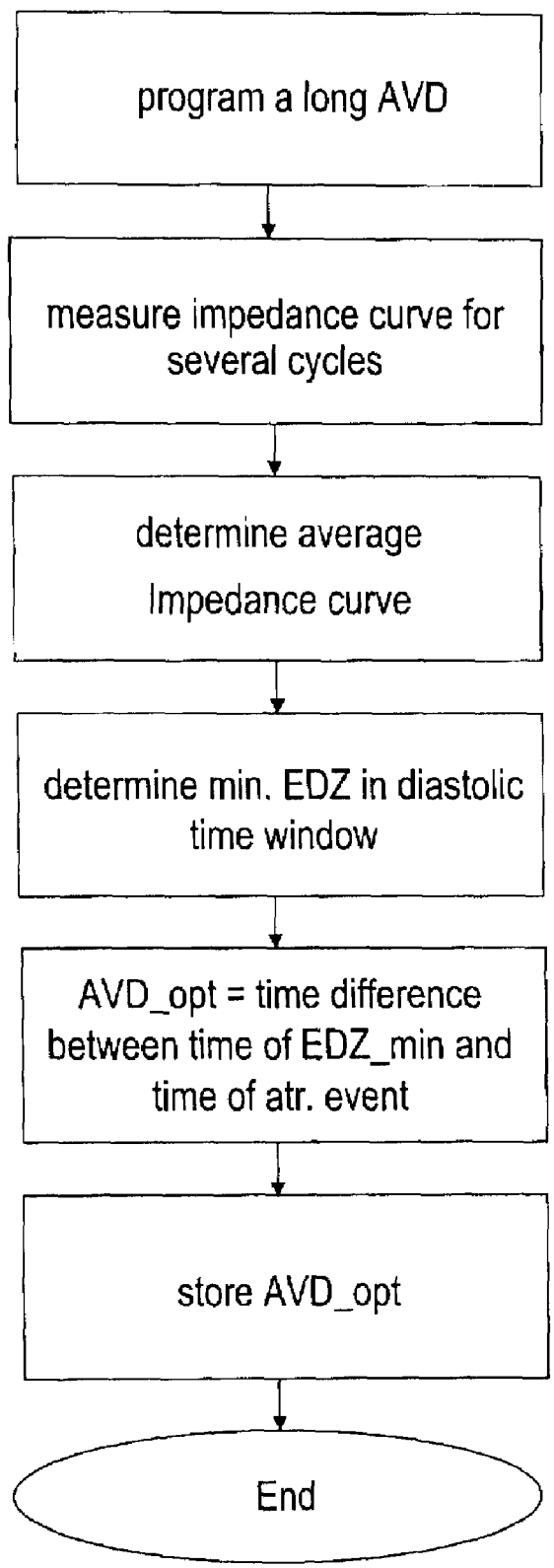
Figure 7:
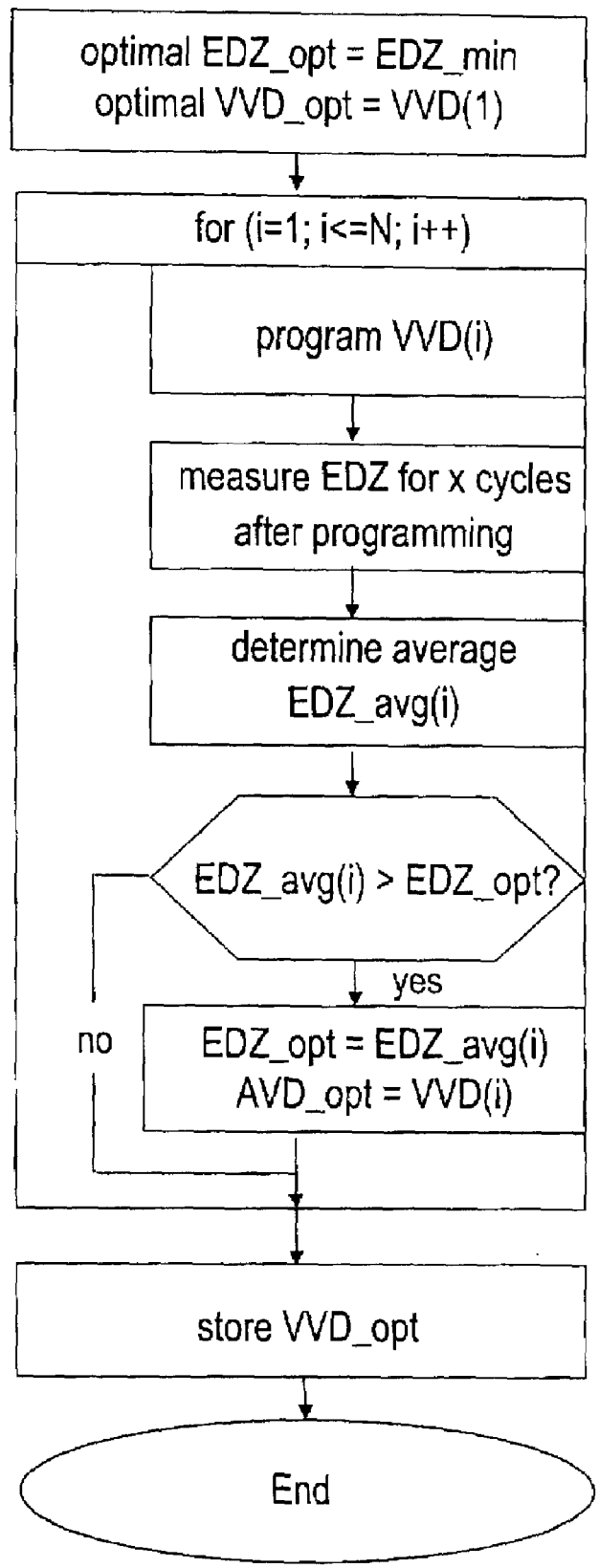
Figure 8:
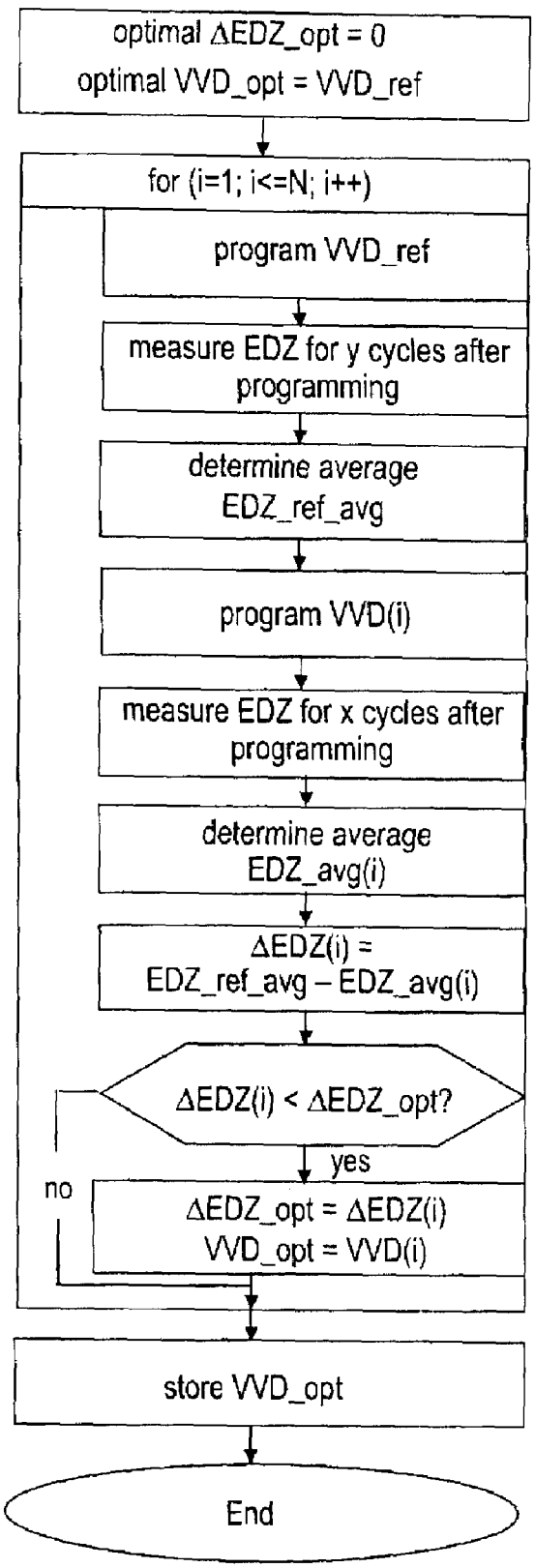

FIG. 1b: a graphical representation of a measuring current to be delivered in order to measure an intracardiac impedance;

FIG. 2a: is a schematical representation of the main components of the pacemaker from FIG. 1;

FIG. 2b: is a schematical representation of an alternative pacemaker according to FIG. 1;

FIG. 2c: is a schematical representation of a third, alternative embodiment of a pacemaker similar to the pacemaker of FIG. 1;

FIG. 3a. is a schematical representation of an electrocardiogram over more than one heart cycle;

FIG. 3b: shows a typical time cause of an intracardiac impedance in a synoptical representation with respect to time cause of the electrocardiogram from FIG. 3a;

FIG. 3c: is another synoptical representation of the electrocardiogram with respect to the time cause of the left ventricular volume and the left ventricular impedance;

FIG. 4: is a flow charge of a first embodiment of a control unit of a pacemaker according to FIGS. 1 and 2;

FIG. 5: is a block diagram representing an alternative control unit of a pacemaker according to FIGS. 1 and 2;

FIG. 6: is a block diagram illustrating how a third alternative embodiment of a control unit for a pacemaker according to FIGS. 1 and 2 operates;

FIG. 7: is a block diagram illustrating a VVD optimization mode of a control unit for the pacemaker according to FIGS. 1 and 2; and FIG. 8: shows a block diagram of an alternative embodiment of a control unit for optimizing the VVD.

On the left hand side of FIG. 1a a typical, implantable three chamber, biventricular pacemaker 10 is depicted. The invention will be illustrated by way of an example given by such three chamber pacemaker. Of course, the invention is not limited to three chamber pacemakers but can be also realized with dual chamber pacemakers or implantable cardioverters/defibrillators.

Returning now to the three chamber pacemaker 10 of FIG. 1. Pacemaker 10 features metallic housing or can 12 with a header 14 attached to the pacemaker can 12. The header 14 is made from transparent plastic material and houses electrical connectors which are electrically connected to electronic components enclosed within the pacemaker can 12. Three electrode leads are connected to Header 14 by way of matching plugs. One electrode lead is a right atrial electrode lead 16 which carries a right atrial tip electrode 22 an a right atrial ring electrode 24 at its distal end.

A second electrode lead is a right ventricular electrode lead 18 which carries a right ventricular tip electrode 26 at its very distal end and a right ventricular ring electrode 28 close to the right ventricular tip electrode 26.

A third electrode lead is a left ventricular electrode lead 20 carrying a tip electrode 30 and a ring electrode 32 at its distal end. The left ventricular electrode lead 20 is designed as a coronary sinus electrode which passes through the coronary sinus of a human heart and into a lateral vein so that the left ventricular tip electrode 30 and the left ventricular ring electrode 32 a in close proximity to the myocard of the left ventricle of a human heart, when in its implanted state.

The electrical and electronic components enclosed by the pacemaker's can 12 include for example a battery and further components well known to the man skilled in the art.

Those components which are of some relevance for the invention or for preferred embodiments of the invention are displayed in FIGS. 2a, 2b and 2c.

One of the components of pacemaker 10 is an impedance measuring stage IMP which is operatively connected to a measuring current generator I and a voltage measuring unit U. The measuring current generator has its two poles connected to different connectors for different electrodes as for example the right ventricular tip electrode and the right ventricular ring electrode (FIGS. 2a and 2c) or the left ventricular ring electrode and the right ventricular ring electrode (FIG. 2b). The voltage measuring unit U has two poles connected to, for example, a connector for the left ventricular tip electrode and the left ventricular ring electrode (FIG. 2a) or the left ventricular tip electrode and the right ventricular tip electrode (FIG. 2b) or the left ventricular tip electrode and the pacemaker can 12 (FIG. 2c). Thus, a quadropolar impedance measurement configuration is established.

Impedance measurement is carried out by injecting a constant current and sampling the resulting voltage.

The measuring current is preferably pulsed, as depicted in FIG. 1b. Typically, the measuring current will feature biphasic pulses wherein two constant current pulses of opposite polarity form one pulse package. Between two consecutive pulse packages a time gap is provided, which is significantly longer than the duration of one pulse package. The constant current pulses within one pulse package are each of the same intensity and of same duration. They only have different polarities. The typical value for the intensity of the constant current pulses is between 50 µA and 600 µA. The typical pulse duration of a single constant current pulse is about 15 µs.

The time gap between each two consecutive pulse packages may be 500 times longer than the duration of one constant current pulse. Other than depicted in FIG. 1, the two constant current pulses of opposite polarity within one pulse package may not follow immediately each other but may have a time gap there between. This time gap however, will be very short compared to the time gap between two consecutive pulse packages. Furthermore, consecutive pulse packages may be face alternating such that a first pulse package for example will begin with a positive constant current pulse whereas the following pulse package will begin with a negative constant current pulse and end with a positive constant current pulse.

The most preferred quadrupolar configuration for impedance measurement is the configuration as depicted in FIG. 2a wherein current injection will occur between right ventricular tip electrode and right ventricular ring electrode and voltage measurement will occur between the left ventricular tip and the left ventricular ring electrode.

In FIG. 3b a typical time course of the left ventricular impedance is depicted. FIG. 3a shows a typical electrocardiogram. When the left ventricle has its smallest volume at the end of the systole (contraction of the ventricle) the impedance has a maximum. As shown in FIG. 3c the time course of the impedance inversely reflects the time course left ventricular volume.

Further components of the pacemakers shown in FIGS. 2a, 2b and 2c are common components of pacemaker like a control unit CTRL, sensing stages (sensing amplifiers) and stimulation pulse generators for each of the heart chambers to be stimulated, namely an atrial sensing stage A-SENS, an atrial stimulation pulse generator A-STIM, a right ventricular sensing stage RV-SENS, a right ventricular stimulation stage RV-STIM, a left ventricular sensing stage LV-SENS and a left ventricular stimulation pulse generator LV-STIM.

The main purpose of the sensing stages is to detect a natural (intrinsic) contraction of the respective heart chamber in order to generate a sense event signal like an atrial sense event As, a right ventricular sense event RVs and a left ventricular sense event LVs. These sense events are processed by the control unit CTRL in order to inhibit a delivery of a stimulation pulse when the pacemaker is operating in a demand mode or in order to determine a time interval between an atrial event and a point of time, when the course of the left ventricular intracardiac impedance reaches its minimum value, see below.

Another type of event to be processed by the control unit CTRL would be the delivery of a stimulation pulse to a respective heart chamber. Delivery of a stimulation pulse causes a paced event such as an atrial paced event Ap, a right ventricular paced event RVp and a left ventricular paced event LVp.

In order to enable the pacemaker to respond to different states of metabolic demand of a patient i.e. to respond to a state of rest or to states of exertion, the pacemaker comprises an activity sensor ACT. The output signal of the activity sensor reflects the metabolic demand of a patient and is used for example to adapt the stimulation rate in order to match the metabolic demand.

According to a preferred embodiment of the invention, different optimal time delays for different stimulation (pacing) rates and thus for different states of metabolic demand are determined. Therefore, a memory MEM is provided and connected to control unit CTRL which is adapted to store optimal time delays such as optimal AV-delays AVD_opt and optimal VV-delays VVD_opt for different states of exertion.

Memory MEM also serves for storing transient values for a measured minimum impedance (end diastolic impedance EDZ) and tested time delays associated therewith as disclosed in more detail further below.

An evaluation unit EVAL acts as a minimum impedance detector and is adapted to determine a minimum impedance value for each heart cycle. For this purpose the evaluation unit EVAL is connected to the impedance measuring stage IMP. Minimum impedance values EDZ for different time delays to be tested are stored in association with said time delays in memory MEM for further processing by the control unit CTRL.

Processing includes deriving average minimum impedance values EDZ_avg and optimal time delays AVD_opt or VVD_opt, respectively.

A telemetry unit TEL is connected to memory MEM and allows to transmit data stored and memory MEM such as minimum impedance values or optimal time delay to a remote central service center.

FIG. 4 shows a flow chart illustrating how the control unit operates when optimizing an AV-delay according to a first embodiment of the invention.

First, initial values for an optimal end diastolic impedance and an AV-delay (AVD) are set:

$$\text{optimal EDZ}_{opt=EDZ\_\max}$$

$$\text{optimal AVD}_{opt=AVD}(1)$$

Then, for a predetermined number of x heart cycles, EDZ is measured while maintaining a first programmed AVD to be tested. Thereafter, an average EDZ is determined from said x EDZ values thus measured.

The average EDZ_avg thus determined is compared to the initial EDZ value. If the average EDZ_avg value is smaller than the initial EDZ value, the AVD associated with the smaller average EDZ_avg is stored as a transient optimal AVD_opt value.

Then, a different AVD to be tested is applied for another number x of heart cycles and another average EDZ_avg is determined while applying said second AVD. The new average EDZ_avg is compared to the previous EDZ_avg. Depending on whether the new average EDZ_avg is smaller than the previous EDZ_avg or not, the previous optimal AVD_opt value is replaced by the latest AVD value or the previous optimal AVD_opt value is maintained, respectively. That procedure is N-times repeated and forms a test procedure to find an optimal AVD. Thus, N different AVD values are tested.

The optimal AVD value AVD_opt thus determined is then applied for further pacing.

Alternatively to the method described above (and below) for calculating EDZ_avg (determining an EDZ for each of the x curves and then calculating an average EDZ_avg from the x individual EDZ values), an average impedance curve may be determined from x single impedance curves and then the EDZ_avg may be calculated from this averaged impedance curve.

When carrying out said test procedure, the control unit searches the optimal AVD_opt that corresponds with the maximum LVEDV, i.e., with the minimum EDZ. N is a number of predefined AVD values, e.g., in a list. Each AVD must be smaller than the intrinsic conduction time if present and ensure effective ventricular pacing without fusion or pseudo-fusion. The AVD values in the list must not necessarily be in a numeric order, but e.g. could be ordered in a random manner. x is the number of heart cycles required for EDZ averaging.

The test procedure is repeated periodically so that the AVD is optimized under all different physiologic conditions, e.g., for rest and for exertion. Different optimal AVD settings are determined for intrinsic and for paced atrial events and for different rate bins. The determined optimal AVD_opt during each run of the algorithm is stored into the related rate bin in memory MEM, i.e., it is assigned to that heart rate under which it was determined.

Alternatively AVD_opt may be averaged or filtered into the rate bin, i.e., filtered or averaged with previously computed values. The complete optimal dynamic AVD function is determined this way. It is paced according to the stored AVD values.

In an alternative embodiment as shown in the flow chart of FIG. 5, the control unit is adapted to carry out a modified test procedure, wherein the optimal AVD is determined by transitioning between a reference measurement and the test measurement. For said reference measurement, a fixed reference AV-delay AVD_ref is applied and average EDZ value EDZ_ref_avg is determined over y heart cycles.

Immediately following the reference measurement, a test measurement wherein an AV-delay to be test is applied, is carried out over x heart cycles and thus an average EDZ value EDZ_avg is determined; see flowchart FIG. 5. Then, the difference ΔEDZ between EDZ_ref_avg and EDZ_avg is determined.

The modified test procedure according to FIG. 5 always including said reference measurement and said test measurement is repeated N times in order to test N different values of AVD. That AVD value in a maximum ΔEDZ (because EDZ_avg is minimal) is stored as optimal AVD_opt.

The modified test procedure according to FIG. 5 is similar to the test procedure according to FIG. 4. The difference is, that a reference measurement with a fixed reference AVD_ref is carried out between testing the different AVD(i) in a test measurement. The reference measurement is a baseline measurement which is performed before each AVD(i). The baseline EDZ_ref is averaged for y heart cycles to determine EDZ_ref_avg. According to the test procedure of FIG. 5 the criterion for optimization is not the absolute EDZ (as in FIG. 4) but the deviation from the reference value. The advantage of the alternative test procedure according to FIG. 5 is, that it automatically follows physiological changes that interfere with the optimization procedure, e.g., exertion of the patient.

In a third alternative embodiment the control unit is adapted to carry out a test procedure as represented by the flow chart of FIG. 6. This test procedure is based on the same principle as the first two procedures, i.e., the maximization of the LVEDV.

Instead of varying the AVD and searching for the lowest EDZ, in this case the optimal AVD is directly determined from the impedance signal course or from the averaged signal course, respectively.

According to the third alternative test procedure, an impedance curve is measured for several cycles and an average impedance curve is determined. Then the time interval from an atrial event (intrinsic (sensed) or stimulated (paced) atrial contraction) to the point of time when the average impedance curve reaches its minimum EDZ_min is determined and assigned as value for the optimal AV delay AVD_opt:

AVD_opt=time difference between time of EDZ_min and time of atrial event

Initially it is paced with a long AVD that ensures effective ventricular pacing. The complete impedance wave is recorded for some cycles. From the average signal wave the time when the EDZ is minimal is determined. It is searched for a local EDZ minimum within a certain diastolic time window. The optimal AVD is computed from the time difference between the time of occurrence of the minimal EDZ and the time of the atrial event. The procedure is repeated periodically so that the AVD is optimized under all different physiologic conditions.

A further improvement of the test procedure according to FIG. 6 is to additionally consider the electromechanical delay of the ventricular stimulation. The mechanical contraction of the ventricular myocardium usually is delayed by a certain period after the ventricular stimulus has been delivered. I.e., the disadvantage of the test procedure according to FIG. 6 is, that even if the stimulus is delivered at the proper time, the mechanical contraction and hence the blood flow may be delayed.

Two algorithmic methods are proposed to overcome this potential weakness by consideration of the physiologic electromechanical delay:

A constant delay period is subtracted from the optimal AVD value. The delay value may be determined, e.g., from echocardiography, for each patient individually, or set to a predetermined value.

The individual electromechanical delay is determined from an additional impedance measurement with a short AVD. If the ventricle is paced with a very short AVD, that is smaller than the optimal value, it contracts while the blood from the atrium is still flowing into the ventricle. I.e., the closure of the atrioventricular valves interrupts the ventricular filling. In this case the time difference between the delivery of the ventricular stimulus and the occurrence of the minimum of the impedance wave, i.e., the EDZ, reflects the electromechanical delay and is used for shortening the optimal AVD.

Now, two embodiments of a control unit for optimizing an interventricular delay (VVD) are illustrated by way of example.

It is to be appreciated that the control unit CTRL may incorporate both, a test procedure for optimizing an AV-delay according to one of FIGS. 4 to 6 and a test procedure for optimizing an VV-delay according to FIG. 7 or 8.

A first embodiment of a VVD-test procedure is illustrated by the flowchart in FIG. 7. This test procedure essentially resembles the AVD test procedure according to FIG. 4 so essentially the same detailed description applies when AVD is replaced by VVD. Instead of an EDZ—minimum, for VVD—optimization an EDZ—maximum is searched for.

When performing said first VVD test procedure, the control unit searches the optimal VVD_opt with the minimum LVEDV, i.e., with the maximum EDZ. N is a number of predefined VVD values in a list. The VVD values must not necessarily be in a numeric order, but e.g. could be ordered in a random manner. x is a small number of heart cycles required for EDZ averaging. The list may include positive, negative, and 'infinite' (i.e., pacing one chamber only) values. The VVD test procedure according to FIG. 7 is repeated periodically so that the VVD is optimized under all different physiologic conditions, e.g., for rest and for exertion. The optimal VVD_opt is stored or filtered or averaged with the previously determined values. The optimal VVD values may be determined in dependence of the heart rate similar to the AVD optimization methods.

In analogy to the AVD optimization methods VVD optimization can be improved by a transient VVD test procedure as shown in FIG. 8. The alternative VVD test procedure according to FIG. 8 essentially equals the AVD test procedure of FIG. 5 except for the time delay to be tested being a VV-delay instead of a AV-delay, and the search for an EDZ—maximum instead of and EDZ—minimum.

Before each VVD(i) value is tested, it is switched to a baseline value VVD_ref as reference. The smallest difference value between the baseline EDZ and the EDZ of the test value, usually a negative difference, is considered to be optimal.

The optimal AVD and VVD settings, that are automatically adjusted by the implant, are recorded over time in an implant trend memory being part of memory MEM. The trend recordings retrospectively reveal information about the state of the individual circulatory system and possible improvements or exacerbations under a certain therapy. Additionally the optimized values are transmitted via telemetry unit TEL to a service center, e.g., on a daily basis, for instantaneous observation of the patient.

The invention claimed is:

1. A cardiac pacemaker including:
   a. at least one stimulation pulse generator (A-STIM, RV-STIM, LV-STIM) selectively generating a stimulation pulse for delivery to one of at least two different chambers of a heart, the chambers including right and left atria and right and left ventricles,
   b. at least one impedance measuring stage (I, U, IMP), the impedance measuring stage being connectable to electrodes, and measuring an intracardiac impedance when in use,
   c. a control unit (CTRL) connected to the stimulation pulse generator and to the impedance measuring stage, the control unit being adapted to:
      (1) process a minimum impedance value for a heart cycle or for an impedance curve averaged over several heart cycles,
      (2) trigger stimulation pulses for two different chambers of the heart with an adjustable time delay (VVD, AVD), and
      (3) adjust the time delay depending upon the measured intracardiac impedance minimum value,
   wherein the control unit is adapted to adjust the time delay such that the minimum value of the intracardiac impedance during one heart cycle is minimized.

2. The cardiac pacemaker of claim 1 further comprising a minimum impedance detector adapted to detect a minimum impedance during one heart cycle.

3. The cardiac pacemaker of claim 1 wherein the impedance measuring stage is adapted to perform an impedance measurement in a quadrupolar configuration using two poles for current injection and two other poles for voltage measurement.

4. The cardiac pacemaker of claim 1 wherein the control unit is adapted to perform a test measurement wherein an average minimum impedance value (EDZ_avg) is determined for a time delay (i) to be tested by:
 a. applying the time delay (AVD(i); VVD(i)) to be tested for a predetermined number of cardiac cycles;
 b. measuring the minimum impedance value thus achieved for each cardiac cycle; and
 c. forming an average minimum impedance value (EDZ avg) from the measured minimum impedance value associated with the time delay to be tested.

5. The cardiac pacemaker of claim 4 wherein the control unit is adapted to perform several test measurements for different time delays to be tested.

6. The cardiac pacemaker of claim 5 wherein the control unit is adapted to:
 a. compare different average minimum impedance values associated with different time delays, and
 b. determine an optimal time delay being associated with the smallest of all average impedance values (Min(EDZ_avg)) resulting from the test measurements.

7. The cardiac pacemaker of claim 4 wherein the control unit is adapted to perform a reference measurement by which a reference minimum impedance value (EDZ_avg) is determined for a fixed reference time delay by:
 a. applying the reference time delay (AVD_ref; VVD_ref) for a predetermined number y of cardiac cycles,
 b. measuring the minimum impedance value (EDZ_ref) thus achieved for each cardiac cycle, and
 c. forming an average reference minimum impedance value (EDZ_ref_avg) from the measured minimum impedance value associated with the fixed reference time delay.

8. The cardiac pacemaker of claim 7 wherein the control unit is adapted to:
 a. perform a test procedure including a reference measurement and a test measurement, and
 b. determine a difference impedance value ($\Delta$EDZ) between:
  (1) the reference average minimum impedance value (EDZ_ref_avg) resulting from the reference measurement, and
  (2) the average minimum impedance value (EDZ_avg) resulting from the test measurement being associated with a time delay to be tested.

9. The cardiac pacemaker of claim 8 wherein the control unit is adapted to:
 a. repeat the test procedure for different time delays to be tested and to compare different of the difference impedance values ($\Delta$EDZ) associated with different time delays to be tested, and
 b. determine an optimal time delay being associated with the largest of all difference impedance values (Max($\Delta$-EDZ)) resulting from the test procedures.

10. The cardiac pacemaker of claim 1 wherein the time delay is the atrioventricular delay time (AVD).

11. The cardiac pacemaker of claim 1 wherein:
 a. the two different chambers of the heart are a right ventricle and a left ventricle, and
 b. the time delay to be adjusted is an interventricular time delay (VVD).

12. The cardiac pacemaker of claim 1 wherein:
 a. the two different chambers of the heart are a right atrium and a ventricle, and
 b. the time delay to be adjusted is an atrioventricular time delay (AVD).

13. The cardiac pacemaker of claim 12 wherein the control unit is adapted to perform an AVD test procedure including the steps of:
 a. forming an average impedance curve,
 b. determining the duration of a time interval from an atrial event to the point of time when the average impedance curve reaches its minimum, and
 c. assigning the time duration as value for the optimal atrioventricular time delay (AVD_opt).

14. A cardiac pacemaker including:
 a. a stimulation pulse generator capable of generating a stimulation pulse for delivery to a chamber of a heart;
 b. an impedance measuring stage capable of measuring an intracardiac impedance;
 c. a control unit in communication with the stimulation pulse generator and the impedance measuring stage, wherein the control unit:
  (1) processes a minimum intracardiac impedance value over one or more heart cycles,
  (2) issues heart stimulation pulses having an adjustable time delay; and
  (3) adjusts the time delay such that the minimum value of the intracardiac impedance during one heart cycle is minimized.

15. The cardiac pacemaker of claim 14 wherein the time delay is the atrioventricular delay time (AVD).

16. A cardiac pacemaker method comprising the steps of:
 a. measuring an intracardiac impedance;
 b. processing a minimum intracardiac impedance value over one or more heart cycles,
 c. triggering stimulation pulses for different heart chambers, the stimulation pulses having a time delay:
  (1) dependent upon the minimum intracardiac impedance value, and
  (2) adjusted such that the minimum intracardiac impedance value during one heart cycle is minimized.

17. The cardiac pacemaker of claim 16 wherein the time delay is the atrioventricular delay time (AVD).

* * * * *